United States Patent [19]

van den Bosch et al.

[11] Patent Number: 4,477,678

[45] Date of Patent: Oct. 16, 1984

[54] SULFUR-CONTAINING FLAVORING AGENTS

[75] Inventors: Steven van den Bosch, Wondenberg; Dirk K. Kettenes, Putten; Kris B. de Roos, Hoevelaken; Gerben Sipma, Hoevelaken; Jan Stoffelsma, Hoevelaken, all of Netherlands

[73] Assignee: P.F.W. Beheer B.V., Netherlands

[21] Appl. No.: 455,619

[22] Filed: Jan. 4, 1983

Related U.S. Application Data

[60] Division of Ser. No. 908,492, May 22, 1978, Pat. No. 4,380,655, which is a division of Ser. No. 762,534, Jan. 26, 1977, Pat. No. 4,119,737, which is a continuation of Ser. No. 531,274, Dec. 10, 1974, abandoned.

[30] Foreign Application Priority Data

Dec. 13, 1973 [GB] United Kingdom ............. 57908/73

[51] Int. Cl.³ ................. C07D 333/00; C07D 311/72; A23L 2/26
[52] U.S. Cl. ........................................ 549/62; 549/60; 549/472; 549/475; 426/535; 426/536
[58] Field of Search ................. 549/472, 60, 62, 475

[56] References Cited

U.S. PATENT DOCUMENTS

| | | | |
|---|---|---|---|
| 3,666,495 | 5/1972 | Evers | 549/472 |
| 4,119,737 | 10/1978 | Bosch et al. | 549/472 |
| 4,380,655 | 4/1983 | Bosch et al. | 549/60 |

Primary Examiner—Alan Siegel

[57] ABSTRACT

Novel thioether compounds are disclosed which are useful as flavoring materials to enhance or impart meat-like flavors to foodstuffs. These compounds have the general formula

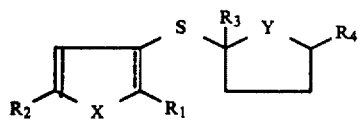

where X can be, under specified conditions, $-CH_2-$, oxygen, or sulfur, Y can be oxygen or sulfur and $R_1$, $R_2$, $R_3$, and $R_4$ are hydrogen or 1 to 3 carbon alkyl groups.

8 Claims, No Drawings

SULFUR-CONTAINING FLAVORING AGENTS

This is a division of application Ser. No. 908,492, filed May 22, 1978 now U.S. Pat. No. 4,380,655 which was a division of application Ser. No. 762,534 filed Jan. 26, 1977 now U.S. Pat. No. 4,119,737, which was a continuation of application Ser. No. 531,274, filed Dec. 10, 1974 now abandoned.

The invention relates to new sulfur-containing flavoring agents (olafactory and gustatory agents) which possess interesting and unexpected organoleptic properties and which therefore are useful in a great variety of flavoring compositions.

More particularly they are useful for enhancing the meat flavor of meat products or meat-containing foods and for imparting a meat flavor to non-meat foods.

The compounds of the invention are thioethers which are generically represented by the following general structural formula

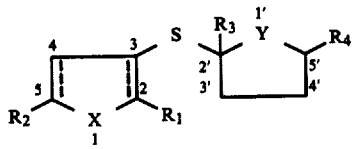

wherein
the X-containing ring is a member selected from the class consisting of
(a) the cyclopentane ring
(b) the Δ²,³-cyclopentene ring
(c) the tetrahydrofuran ring
(d) the tetrahydrothiophene ring
(e) the 4,5-dihydrofuran ring
(f) the 4,5-dihydrothiophene ring
(g) the furan ring; and
(h) the thiophene ring;
Y is selected from the class consisting of oxygen and sulfur; and $R_1$, $R_2$, $R_3$ and $R_4$ are selected from the class consisting of hydrogen and 1 to 3 carbon alkyl groups.

The compounds of the invention are sub-classified hereinafter by the structural formulae

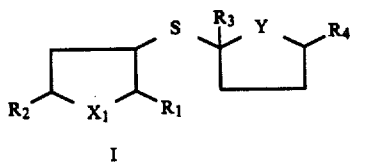

I

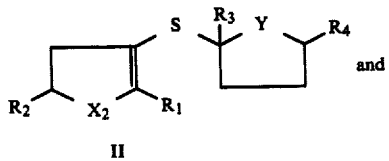

II

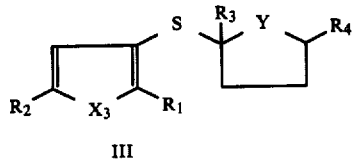

III wherein $X_1$ and $X_2$ represent a —$CH_2$— group, oxygen or sulfur, $X_3$ represents oxygen or sulfur, and Y, $R_1$, $R_2$, $R_3$ and $R_4$ are as specified above.

When the X-containing ring in the above formula is a cyclopentane or cyclopentene ring ($X_1$ or $X_2$ is —$CH_2$—), preferred materials according to the invention are those wherein $R_1$ is hydrogen or a 1 to 3 carbon alkyl group, $R_2$ is hydrogen, $R_4$ is hydrogen or methyl, and $R_3$ is methyl. When the X-containing ring is one of the above-recited heterocyclic rings ($X_1$, $X_2$ or $X_3$ is oxygen or sulfur), $R_1$ and $R_3$ are preferably methyl and $R_2$ and $R_4$ are preferably methyl or hydrogen.

The present invention also includes in its scope flavoring and flavor enhancing compositions containing the aforedescribed compounds and foodstuffs and food compositions containing such compounds.

It will be understood that most of the new compounds of the invention can exist in various geometric isomeric forms, and formulae given herein include such isomers. Specific representatives of the new compounds included within the foregoing structural formula are listed in Table I.

Although many examples of furyl-, dihydrofuryl-, and tetrahydrofurylsulfides and mercaptans and also the corresponding thienyl mercaptans as well as some cyclopentyl mercaptans are known as flavoring agents in the patent literature (British Pat. Nos. 1,283,912 and 1,354,431; U.S. Pat. Nos. 3,666,495, 3,677,772 and 3,723,475), there is no mention in the prior art of analogous compounds with a sulfide linkage between a cyclopentane/cyclopentene ring and an alpha-carbon atom of a tetrahydrofuran or a tetrahydrothiophene ring, and of analogous compounds with a sulfid linkage between a beta-carbon atom and an alpha-carbon atom of two heterocyclic five-membered ring systems. Although the compounds of the invention are mercaptals and monothioacetals, they are surprisingly stable towards hydrolysis and elevated temperatures.

The new compounds of the invention can be prepared by methods known per se, by addition of a mercaptan to a cyclic vinyl ether or vinyl thioether. As an example of such a method, the new compounds exemplified by formula I may be prepared according to the following reaction scheme:

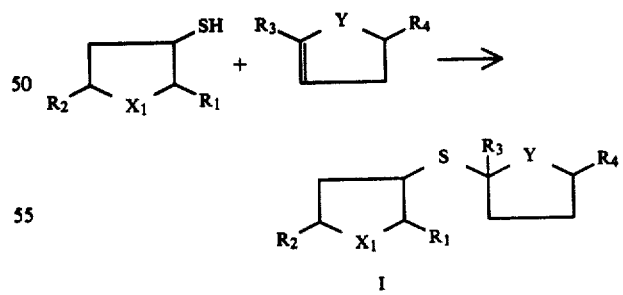

I wherein $X_1$, Y, $R_1$, $R_2$, $R_3$ and $R_4$ possess the aforedescribed meaning.

The addition reaction can be conducted in the presence of a catalytical amount of acid and with or without a solvent. A variety of solvents can be used; hydrocarbons such as pentane, ethers such as diethyl ether, tetrahydrofuran, etc. As acids can be used p-toluenesulfonic acid, thionyl chloride, gaseous hydrogen chloride, etc. The addition can be effected at room temperature or at slightly elevated temperatures, say, at the reflux temperature of the solvent.

products or meat-containing foods and to impart a meat flavour to non-meat foods.

TABLE I

| NAME | CLASS | $R_1$ | $R_2$ | $R_3$ | $R_4$ | X | Y | Exp. nr |
|---|---|---|---|---|---|---|---|---|
| 2-methyl-3-(2'-methyl-2'-tetrahydrofurylthio)tetrahydrofuran | I | $CH_3$ | H | $CH_3$ | H | O | O | 1 |
| 2-methyl-3-(2'-methyl-2'-tetrahydrothienylthio)tetrahydrofuran | I | $CH_3$ | H | $CH_3$ | H | O | S | 1c |
| 2-methyl-3-(2',5'-dimethyl-2'-tetrahydrofurylthio)tetrahydrofuran | I | $CH_3$ | H | $CH_3$ | $CH_3$ | O | O | 3f |
| 2-methyl-3-(2'-methyl-2'-tetrahydrofurylthio)tetrahydrothiophene | I | $CH_3$ | H | $CH_3$ | H | S | O | 2d |
| 2-methyl-3-(2'-methyl-2'-tetrahydrothienylthio)tetrahydrothiophene | I | $CH_3$ | H | $CH_3$ | H | S | S | 3c |
| 2-methyl-3-(2',5'-dimethyl-2'-tetrahydrofurylthio)tetrahydrothiophene | I | $CH_3$ | H | $CH_3$ | $CH_3$ | S | O | 3i |
| 5-isopropyl-2-methyl-3-(2'-methyl-2'-tetrahydrofurylthio)tetrahydrothiophene | I | $CH_3$ | iso-$C_3H_7$ | $CH_3$ | H | S | O | 2e |
| 2,5-dimethyl-3-(2'-methyl-2'-tetrahydrofurylthio)tetrahydrofuran | I | $CH_3$ | $CH_3$ | $CH_3$ | H | O | O | 2a |
| 2,5-dimethyl-3-(2'-methyl-2'-tetrahydrothienylthio)tetrahydrofuran | I | $CH_3$ | $CH_3$ | $CH_3$ | H | O | S | 3a |
| 2,5-dimethyl-3-(2',5'-dimethyl-2'-tetrahydrofurylthio)tetrahydrofuran | I | $CH_3$ | $CH_3$ | $CH_3$ | $CH_3$ | O | O | 2k |
| (2'-methyl-2'-tetrahydrofurylthio)cyclopentane | I | H | H | $CH_3$ | H | $CH_2$ | O | 3k |
| 2-methyl-1-(2'-methyl-2'-tetrahydrofurylthio)cyclopentane | I | $CH_3$ | H | $CH_3$ | H | $CH_2$ | O | 3 |
| 2-ethyl-1-(2'-methyl-2'-tetrahydrofurylthio)cyclopentane | I | $C_2H_5$ | H | $CH_3$ | H | $CH_2$ | O | 3m |
| 2-methyl-3-(2'-methyl-2'-tetrahydrofurylthio)-4,5-dihydrofuran | II | $CH_3$ | H | $CH_3$ | H | O | O | 1a |
| 2-methyl-3-(2'-methyl-2'-tetrahydrothienylthio)-4,5-dihydrofuran | II | $CH_3$ | H | $CH_3$ | H | O | S | 2h |
| 2-methyl-3-(2',5'-dimethyl-2'-tetrahydrofurylthio)-4,5-dihydrofuran | II | $CH_3$ | H | $CH_3$ | $CH_3$ | O | O | 3g |
| 2-methyl-3-(2'-methyl-2'-tetrahydrofurylthio)-4,5-dihydrothiophene | II | $CH_3$ | H | $CH_3$ | H | S | O | 2f |
| 2-methyl-3-(2'-methyl-2'-tetrahydrothienylthio)-4,5-dihydrothiophene | II | $CH_3$ | H | $CH_3$ | H | S | S | 3d |
| 2-methyl-3-(2',5'-dimethyl-2'-tetrahydrofurylthio)-4,5-dihydrothiophene | II | $CH_3$ | H | $CH_3$ | $CH_3$ | S | O | 3j |
| 2,5-dimethyl-3-(2'-methyl-2'-tetrahydrofurylthio)-4,5-dihydrofuran | II | $CH_3$ | $CH_3$ | $CH_3$ | H | O | O | 2b |
| 2,5-dimethyl-3-(2'-methyl-2'-tetrahydrothienylthio)-4,5-dihydrofuran | II | $CH_3$ | $CH_3$ | $CH_3$ | H | O | S | 2i |
| 2,5-dimethyl-3-(2',5'-dimethyl-2'-tetrahydrofurylthio)-4,5-dihydrofuran | II | $CH_3$ | $CH_3$ | $CH_3$ | $CH_3$ | O | O | 3h |
| (2'-methyl-2'-tetrahydrofurylthio)-1-cyclopentene | II | H | H | $CH_3$ | H | $CH_2$ | O | 3n |
| 2-methyl-1-(2'-methyl-2'-tetrahydrofurylthio)-1-cyclopentene | II | $CH_3$ | H | $CH_3$ | H | $CH_2$ | O | 3l |
| 2-methyl-3-(2'-methyl-2'-tetrahydrofurylthio)furan | III | $CH_3$ | H | $CH_3$ | H | O | O | 1b |
| 2-methyl-3-(2'-methyl-2'-tetrahydrothienylthio)furan | III | $CH_3$ | H | $CH_3$ | H | O | S | 1d |
| 2-methyl-3-(2',5'-dimethyl-2'-tetrahydrofurylthio)furan | III | $CH_3$ | H | $CH_3$ | $CH_3$ | O | O | 2j |
| 2-methyl-3-(2'-methyl-2'-tetrahydrofurylthio)thiophene | III | $CH_3$ | H | $CH_3$ | H | S | O | 2g |
| 2-methyl-3-(2'-methyl-2'-tetrahydrothienylthio)thiophene | III | $CH_3$ | H | $CH_3$ | H | S | S | 3e |
| 2-methyl-3-(2',5'-dimethyl-2'-tetrahydrofurylthio)thiophene | III | $CH_3$ | H | $CH_3$ | $CH_3$ | S | O | 2 |
| 2,5-dimethyl-3-(2'-methyl-2'-tetrahydrofurylthio)furan | III | $CH_3$ | $CH_3$ | $CH_3$ | H | O | O | 2c |
| 2,5-dimethyl-3-(2'-methyl-2'-tetrahydrothienylthio)furan | III | $CH_3$ | $CH_3$ | $CH_3$ | H | O | S | 3b |
| 2,5-dimethyl-3-(2',5'-dimethyl-2'-tetrahydrofurylthio)furan | III | $CH_3$ | $CH_3$ | $CH_3$ | $CH_3$ | O | O | 2l |

It is preferred to carry out the addition reaction in a nitrogen atmosphere with pentane as a solvent and a catalytical amount of p-toluenesulfonic acid.

The starting mercaptans such as tetrahydrofuryl-, 4,5-dihydrofuryl-, tetrahydrothienyl-, and 4,5-dihydrothienylmercaptans can be prepared as described in British Patent 1,283,912. The starting mercaptans such as 3-furyl and 3-thienylmercaptans can easily be prepared from the corresponding halo compounds according to the procedure described by L. Brandsma and H. J. T. Bos, Rec.Trav.Chim.Pays-Bas 88, 732 (1969). The cyclopentanethiols can be prepared from the corresponding cyclopentenes, by free radical addition of thioacetic acid followed by hydrolysis according to the procedure described by F. G. Bordwell and W. A. Hewett, J.Amer.Chem.Soc. 79, 3493 (1957). The cyclopentenethiols can be prepared from the corresponding cyclopentanones as described by M. Demuynick and J. Vialle, Bull.Soc.Chim.Fr. 1967, 2748.

The starting 4,5-dihydrofurans can be prepared according to the procedure described by A. Lipp, Chem.Ber. 22, 1199 (1889) and D. H. Aten Armitage and C. L. Wilson J.Amer.Chem.Soc. 81, 2437 (1954). The starting 4,5-dihydrothiophenes can be prepared by the procedure described by M. A. Gianturco, P. Friedel and N. Flanagan, Tetrahedron Lett. 23, 1847 (1965). Purification of the mixture of double bond isomers by liquid chromatography resulted in the isolation of the pure 4,5-dihydrothiophenes.

It has been found that the compounds of the present invention have very characteristic and unexpected organoleptic properties. Even at very low concentrations they can be used for enhancing the meat flavour of meat products or meat-containing foods and to impart a meat flavour to non-meat foods.

The compounds are active in a concentration lower than 0.1 part per million (ppm) in the finished food; for meat type flavours the limits of a practical dosage can vary from 0.01 ppm to 10 ppm in the finished food.

It will be understood that the term flavouring composition as used herein means a material which has flavour notes reminiscent of cooked, fried, or roasted meat such as beef, pork, chicken, or ham, so that it can be used in the preparation of gravies, soups, fish meal, soya and other non-muscle protein containing—processed foods, salad dressing, cream sauce, dip sauces and other meat and non-meat foods.

Although the compounds of the present invention have flavours that can be described as meat-like, it should be explicitly stated that their application is a very wide one and not restricted to flavour compositions imparting meat aromas to roods. It has been found that the compounds of the present invention are also valuable components in flavour compositions of other types that can be characterized as, or associated with flavour types of foodstuffs of animal origin and even certain vegetable types like e.g. maple or nuts. The compounds of the present invention can be used either in pure form or, sometimes more practically as mixtures of some of the members described.

The following examples are only intended to illustrate the invention, but not to limit the same in any way.

EXPERIMENTAL PART

NMR Spectra were recorded on a Jeol C60H, 60 MHz instrument, as solutions in $CCl_4$, with TMS as internal standard.

IR Spectra were measured with a Perkin-Elmer 225, neat or as solutions in $CCl_4$.

Mass Spectra were determined on an AEI MS9 double-focusing (Nier-Johnson) mass spectrometer, at 70 eV, source temperature 150° C. The ten strongest peaks are given, the first one being the base peak (100%).

EXAMPLE 1

Preparation of 2-methyl-3-(2'-methyl-2'-tetrahydrofurylthio)tetrahydrofuran (I; $R_1=CH_3$, $R_2=H$, $R_3=CH_3$, $R_4=H$, $X=O$, $Y=O$)

In a three-necked 250 ml round bottomed flask provided with a mechanical stirrer, dropping funnel, reflux condenser, and thermometer are placed 2.15 g (0.025 mole) of 4,5-dihydro-2-methylfuran in 30 ml of diethyl ether and a trace of p-toluenesulfonic acid. The reaction is carried out under nitrogen. The stirrer is started and a solution of 3.00 g (0.025 mole) of 2-methyl-3-mercapto-tetrahydrofuran (mixture of cis and trans isomer) in 10 ml of diethyl ether is added in 30 minutes. The reaction mixture is heated and allowed to reflux for four hours. After cooling to room temperature, the reaction mixture is made alkaline with 1 ml of triethylamine.

Distillation of the reaction mixture yielded the title compound as a mixture of cis and trans isomers; bp. 65°–68° C./2 mm Hg.

Spectral data:

NMR spectrum ($\delta$ in ppm) of mixture of cis and trans isomers:

$\delta = 1.24$ (d, 3H),
$\delta = 1.67$ (s, 3H),
$\delta = 1.7$–3.0 (m, 7H),
$\delta = 3.2$–4.3 (m, 5H).

IR spectrum (after separation of cis and trans isomers by preparative gas chromatography)

trans isomers in $CCl_4$: 1440, 1373, 1350, 1184, 1099, 1035, 1014, 900, 859, 561 $cm^{-1}$ cis isomers in $CCl_4$: 1440, 1371, 1349, 1182, 1133, 1097, 1064, 1030, 1019, 560 $cm^{-}$ MS spectrum (m/e): 41, 43, 74, 84, 39, 55, 83, 45, 118, 85.

According to the procedure described in Example 1 the following compounds have been prepared:

(a)
2-methyl-3-(2'-methyl-2'-tetrahydrofurylthio)-4,5-dihydrofuran (II; $R_1=CH_3$, $R_2=H$, $R_3=CH_3$, $R_4=H$, $X=O$, $Y=O$)

Addition reaction of 2-methyl-3-mercapto-4,5-dihydrofuran and 4,5-dihydro-2-methylfuran.

Spectral data after purification by liquid chromatography:

| NMR spectrum ($\delta$ in ppm) | |
|---|---|
| $\delta = 1.55$ (s, 3H) | IR spectrum in $CCl_4$ |
| $\delta = 1.87$ (t, 3H) | 2970, 2920, 2885, 1643, 1437, 1378, 1214, |
| $\delta = \sim 1.9$ (m, 4H) | 1100, 1037, 1020, 983, 958, 908, 552, 498, |
| $\delta = 2.8$ (m, 2H) | 440 $cm^{-1}$ |
| $\delta = 3.95$ (m, 2H) | MS spectrum (m/e) |
| $\delta = 4.29$ (t, 2H) | 43, 84, 83, 39, 41, 42, 114, 55, 53, 116 |

(b) 2-methyl-3-(2'-methyl-2'-tetrahydrofurylthio)furan (III; $R_1=CH_3$, $R_2=H$, $R_3=CH_3$, $R_4=H$, $X=O$, $Y=O$)

Addition reaction of 2-methyl-3-mercaptofuran and 4,5-dihydro-2-methylfuran. Spectral data after purification by liquid chromatography:

| NMR spectrum ($\delta$ in ppm) | |
|---|---|
| $\delta = 1.47$ (s, 3H) | IR spectrum |
| $\delta = 2.0$ (m, 4H) | 3120, 2975, 2920, 2880, 1580, 1513, 1440, 1370, |
| $\delta = 2.34$ (s, 3H) | 1222, 1124, 1103, 1086, 1036, 1016, 938, 889, |
| $\delta = 3.95$ (m, 2H) | 732, 656, 606 $cm^{-1}$ |
| $\delta = 6.30$ (d, 1H) | MS spectrum (m/e) |
| $\delta = 7.22$ (d, 1H) | 43, 114, 84, 85, 83, 39, 41, 113, 53, 45 |

(c) Preparation of 2-methyl-3-(2'-methyl-2'-tetrahydrothienylthio)tetrahydrofuran (I; $R_1=CH_3$, $R_2=H$, $R_3=CH_3$, $R_4=H$, $X=O$, $Y=S$)

Addition reaction of 2-methyl-3-mercaptotetrahydrofuran and 4,5-dihydro-2-methylthiophene.

Spectral data of cis and trans isomers after purification by liquid chromatography:

NMR spectrum ($\delta$ in ppm)

| NMR spectrum ($\delta$ in ppm) | | | |
|---|---|---|---|
| trans isomers: | | cis isomers: | |
| $\delta = 1.28$ | (d, 3H) | $\delta = 1.12$ | (d, 3H) |
| $\delta = 1.78$ | (s, 3H) | $\delta = 1.78$ | (s, 3H) |
| $\delta = 1.9$–3.2 | (m, 9H) | $\delta = 2.1$ | (m, 6H) |
| $\delta = 3.3$–4.0 | (m, 3H) | $\delta = 2.9$–4.3 | (m, 6H) |

IR spectrum trans isomers: 2970, 2930, 2860, 1441, 1379, 1352, 1304, 1261, 1230, 1131, 1115, 1080, 1070, 1058, 1016, 944, 860, 666, 468 $cm^{-1}$ cis isomers: 2970, 2930, 2860, 1440, 1373, 1351, 1303, 1261, 1108, 1069, 1056, 1019, 990, 944, 850, 732, 685, 665 $cm^{-1}$ MS spectrum (m/e)

trans isomers: 41, 74, 85, 100, 59, 99, 45, 39, 43, 84, cis isomers: 41, 74, 85, 59, 100, 99, 45, 39, 43, 55.

(d) Preparation of 2-methyl-3-(2'-methyl-2'-tetrahydrothienylthio)furan (III; $R_1=CH_3$, $R_2=H$, $R_3=CH_3$, $R_4=H$, $X=O$, $Y=S$)

Addition reaction of 2-methyl-3-mercaptofuran and 4,5-dihydro-2-methylthiophene.

Spectral data after purification by liquid chromatography:

| NMR spectrum ($\delta$ in ppm) | | |
|---|---|---|
| $\delta = 1.67$ | (s, 3H) | IR spectrum |
| $\delta = 1.8$–2.4 | (m, 4H) | 3115, 2955, 2920, 2855, 1575, 1510, 1437 |
| $\delta = 2.37$ | (s, 3H) | 1382, 1369, 1220, 1120, 1084, 1053, 936, |
| $\delta = 2.98$ | (m, 2H) | 887, 732, 657, 605, 492, $cm^{-1}$ |
| $\delta = 6.33$ | (d, 1H) | MS spectrum (m/e) |
| $\delta = 7.24$ | (d, 1H) | 85, 114, 101, 100, 59, 99, 43, 45, 39, 41 |

EXAMPLE 2

Preparation of 2-methyl-3-(2',5'-dimethyl-2'-tetrahydrofurylthio)thiophene (III; $R_1=CH_3$, $R_2=H$, $R_3=CH_3$, $R_4=CH_3$, $X=S$, $Y=O$)

In a three-necked 250 ml round bottomed flask provided with a mechanical stirrer, dropping funnel, reflux condenser and thermometer are placed 3.34 g (0.034 mole) of 4,5-dihydro-2,5-dimethylfuran in 30 ml diisopropyl ether and a trace of p-toluenesulfonic acid. The reaction is carried out under nitrogen. The stirrer is started and a solution of 4,42 g (0.034 mole) of 2-methyl-3-mercaptothiophene in 10 ml diisopropyl ether is added in 30 minutes. The reaction mixture is heated and allowed to reflux for four hours. After cooling to room temperature, the reaction mixture is poured into a 5% solution of sodium carbonate.

The organic layer is separated and the water layer extracted twice with 30 ml of diisopropyl ether. The organic extract is washed with water and dried over anhydrous sodium sulfate. Distillation gives the title compound as a mixture of isomers; bp. 95°–97° C./2 mm Hg.

Spectral data of the isomers (1 and 2) after purification by liquid chromatography:

| NMR spectrum ($\delta$ in ppm) | | |
|---|---|---|
| 1 $\delta$ = 1,23 (d, 3H) | | IR spectrum |
| $\delta$ = 1,43 (s, 3H) | | 3105, 2970, 2925, 2870, 1442, 1372, 1194, |
| $\delta$ = 2,0 (m, 4H) | | 1143, 1104, 1078, 1033, 961, 940, 885, 885, |
| $\delta$ = 2,50 (s, 3H) | | 825, 709, 626, 546, 477 cm$^{-1}$ |
| $\delta$ = 4,35 (m, 1H) | | MS spectrum (m/e) |
| $\delta$ = 6,94 (s, 2H) | | 43, 130, 98, 97, 129, 83, 55, 39, 45, 41 |
| 2 $\delta$ = 1,28 (d, 3H) | | IR spectrum |
| $\delta$ = 1,44 (s, 3H) | | 3090, 2970, 2925, 2865, 1439, 1369, 1204, |
| $\delta$ = 2,0 (m, 4H) | | 1103, 1061, 1022, 958, 884, 854, 825, 800, |
| $\delta$ = 2,51 (s, 3H) | | 709, 624, 558 cm$^{-1}$ |
| $\delta$ = 4,15 (m, 1H) | | MS spectrum (m/e) |
| $\delta$ = 6,98 (s, 2H) | | 43, 130, 97, 98, 129, 83, 55, 39, 45, 41 |

According to the procedure described in Example 2 the following compounds have been prepared:

(a) Preparation of 2,5-dimethyl-3-(2'-methyl-2'-tetrahydrofurylthio)tetrahydrofuran (I; $R_1$=CH$_3$, $R_2$=CH$_3$, $R_3$=CH$_3$, $R_4$=H, X=O, Y=O)

Addition reaction of 2,5-dimethyl-3-mercaptotetrahydrofuran and 4,5-dihydro-2-methylfuran.

Spectral data after separation by liquid chromatography of the isomeric mixture of the title compound in two mixtures of isomers (1 and 2):

| NMR spectrum ($\delta$ in ppm) | | | | |
|---|---|---|---|---|
| 1 $\delta$ = 1,16 | (d, 3H) | 2 $\delta$ = 1,0–1,3 | (d, 6H) |
| $\delta$ = 1,25 | (d, 3H) | $\delta$ = 1,63 | (s, 3H) |
| $\delta$ = 1,64 | (s, 3H) | $\delta$ = 1,67 | |
| $\delta$ = 1,8–2,1 | (m, 6H) | $\delta$ = 1,8–2,2 | (m, 6H) |
| $\delta$ = 2,80 | (m, 1H) | $\delta$ = 3,4 | (m, 1H) |
| $\delta$ = 3,42 | (m, 1H) | $\delta$ = 3,8–4,4 | (m, 4H) |
| $\delta$ = 3,90 | (m, 3H) | | |

IR spectrum:
1 2975, 2925, 2865, 1443, 1374, 1350, 1190, 1162, 1138, 1101, 1070, 1037, 1021, 949, 880, 832, 564 cm$^{-1}$
2 2975, 2925, 2880, 1460, 1453, 1443, 1375, 1190, 1138, 1103, 1083, 1039, 1020, 942, 916, 880, 810, 565 cm$^{-1}$.
MS spectrum (m/e):
1 55, 43, 54, 88, 84, 99, 83, 39, 73, 60,
2 55, 43, 54, 84, 88, 39, 83, 73, 99, 60.

(b) Preparation of 2,5-dimethyl-3-(2'-methyl-2'-tetrahydrofurylthio)-4,5-dihydrofuran (II; $R_1$=CH$_3$, $R_2$=CH$_3$, $R_3$=CH$_3$, $R_4$=H, X=O, Y=O)

Addition reaction of 4,5-dihydro-2,5-dimethyl-3-mercaptofuran and 4,5-dihydro-2-methylfuran.

Spectral data of the title compound (mixture of isomers) after purification by liquid chromatography:

| NMR spectrum ($\delta$ in ppm) | | |
|---|---|---|
| $\delta$ = 1,30 | (d, 3H) | IR spectrum |
| $\delta$ = 1,52 | (s, 3H) | 2970, 2920, 2865, 1644, 1439, 1375, 1329, |
| $\delta$ = 1,82 | (d, 3H) | 1222, 1188, 1103, 1038, 1017, 954, 902, 821, |
| $\delta$ = 1,8–3,2 | (m, 6H) | 555, 505 cm$^{-1}$ |
| $\delta$ = 3,9 | (m, 2H) | MS spectrum (m/e) |
| $\delta$ = 4,6 | (m, 1H) | 43, 84, 128, 39, 41, 55, 130, 85, 53 |

(c) Preparation of 2,5-dimethyl-3-(2'-methyl-2'-tetrahydrofurylthio)furan (III; $R_1$=CH$_3$, $R_2$=CH$_3$, $R_3$=CH$_3$, $R_4$=H, X=O, Y=O)

Addition reaction of 2,5-dimethyl-3-mercaptofuran and 4,5-dihydro-2-methylfuran.

Spectral data of the title compound after purification by liquid chromatography:

| NMR spectrum ($\delta$ in ppm) | | |
|---|---|---|
| $\delta$ = 1,47 (s, 3H) | | IR spectrum |
| $\delta$ = 1,9 (m, 4H) | | 3115, 2970, 2920, 2875, 1609, 1570, 1440, 1369 |
| $\delta$ = 2,22 (s, 3H) | | 1330, 1220, 1102, 1035, 1018, 922, 800, 654, 6 |
| $\delta$ = 2,27 (s, 3H) | | 557, 492 cm$^{-1}$ |
| $\delta$ = 3,95 (m, 2H) | | MS spectrum (m/e) |
| $\delta$ = 6,37 (s, 1H) | | 43, 39, 128, 41, 84, 85, 55, 53, 42, 83 |

(d) Preparation of 2-methyl-3-(2'-methyl-2'-tetrahydrofurylthio)tetrahydrothiophene (I; $R_1$=CH$_3$, $R_2$=H, $R_3$=CH$_3$, $R_4$=H, X=S, Y=O)

Addition reaction of 2-methyl-3-mercaptotetrahydrothiophene (mixture of cis and trans isomer) and 4,5-dihydro-2-methylfuran.

Spectral data of the title compound as a mixture of cis and trans isomers after purification by liquid chromatography:

| NMR spectrum ($\delta$ in ppm) | | |
|---|---|---|
| $\delta$ = 1,37 (d, 3H) | | IR spectrum |
| $\delta$ = 1,67 (s, 3H) | | 2965, 2925, 2880, 2860, 1440, 1372, 1260, 1191 |
| $\delta$ = 2,00 (m, 6H) | | 1138, 1102, 1037, 1019, 830, 684, 561 cm$^{-1}$ |
| $\delta$ = 2,85 (m, 4H) | | MS spectrum (m/e) |
| $\delta$ = 3,92 (m, 2H) | | 43, 134, 41, 39, 55, 84, 74, 83, 69, 85 |

(e) Preparation of 5-isopropyl-2-methyl-3-(2'-methyl-2'-tetrahydrofurylthio)tetrahydrothiophene (I; $R_1$=CH$_3$, $R_2$=iso-C$_3$H$_7$, $R_3$=CH$_3$, $R_4$=H, X=S, Y=O)

Addition reaction of 5-isopropyl-2-methyl-3-mercaptotetrahydrothiophene (mixture of isomers) and 4,5-dihydro-2-methylfuran.

Spectral data of the title compound as a mixture of isomers after purification by liquid chromatography:

| NMR spectrum ($\delta$ in ppm) | | |
|---|---|---|
| $\delta$ = 0,95 | (d, 6H) | IR spectrum |
| $\delta$ = 1,2–1,4 | (doublets, 3H) | 2965, 2920, 2865, 1450, 1443, 1382, |
| $\delta$ = 1,66 | (s, 3H) | 1371, 1365, 1235, 1190, 1138, 1100, |
| $\delta$ = 2,0 | (m, 7H) | 1036, 1018, 922, 902, 830, 561 cm$^{-1}$ |
| $\delta$ = 2,7–3,6 | (m, 3H) | MS spectrum (m/e) |
| $\delta$ = 3,9 | (m, 2H) | 43, 99, 133, 84, 176, 41, 39, 55, |

-continued

| NMR spectrum (δ in ppm) |
|---|
| 83, 42 |

(f) Preparation of 2-methyl-3-(2'-methyl-2'-tetrahydrofurylthio)-4,5-dihydrothiophene (II; $R_1=CH_3$, $R_2=H$, $R_3=CH_3$, $R_4=H$, $X=S$, $Y=O$)

Addition reaction of 4,5-dihydro-2-methyl-3-mercaptothiophene and 4,5-dihydro-2-methylfuran.

Spectral data of the title compound after purification by liquid chromatography:

| NMR spectrum (δ in ppm) | | |
|---|---|---|
| δ = 1,58 | (s, 3H) | IR spectrum |
| δ = 2,01 | (s, 3H) | 2970, 2920, 2875, 1593, 1439, 1371, 1186, |
| δ = 1,9–2,1 | (m, 4H) | 1145, 1103, 1038, 1018, 924, 903, 840, 754, |
| δ = 3,0–3,3 | (m, 4H) | 695, 561, 521, cm$^{-1}$ |
| δ = 3,95 | (m, 2H) | MS spectrum (m/e) |
| | | 43, 84, 39, 83, 99, 41, 132, 55, 53, 59 |

(g) Preparation of 2-methyl-3-(2'-methyl-2'-tetrahydrofurylthio)thiophene (III; $R_1=CH_3$, $R_2=H$, $R_3=CH_3$, $R_4=X=S$, $Y=O$)

Addition reaction of 2-methyl-3-mercaptothiophene and 4,5-dihydro-2-methylfuran.

Spectral data of the title compound after purification by liquid chromatography:

| NMR spectrum (δ in ppm) | | |
|---|---|---|
| δ = 1,45 (s, 3H) | | IR spectrum |
| δ = 2,0 (m, 4H) | | 3100, 3080, 2970, 2920, 2870, 1436, 1369, 1178 |
| δ = 2,48 (s, 3H) | | 1136, 1102, 1037, 1018, 854, 709, 626, 552, 47 |
| δ = 3,95 (m, 2H) | | 460 cm$^{-1}$ |
| δ = 6,95 (s, 2H) | | MS spectrum (m/e) |
| | | 43, 97, 130, 39, 41, 45, 84, 129, 69, 53 |

(h) Preparation of 2-methyl-3-(2'-methyl-2'-tetrahydrothienylthio)-4,5-dihydrofuran (II; $R_1=CH_3$, $R_2=H$, $R_3=CH_3$, $R_4=H$, $X=O$, $Y=S$)

Addition reaction of 4,5-dihydro-2-methyl-3-mercaptofuran and 4,5-dihydro-2-methylthiophene.

Spectral data of the title compound after purification by liquid chromatography:

| NMR spectrum (δ in ppm) | | |
|---|---|---|
| δ = 1,70 | (s, 3H) | IR spectrum |
| δ = 1,90 | (t, 3H) | 2955, 2920, 2860, 1636, 1436, 1378, 1303, |
| δ = 2,0–2,4 | (m, 4H) | 1216, 1053, 983, 959, 909, 491, 470 cm$^{-1}$ |
| δ = 2,6–3,1 | (m, 4H) | MS spectrum (m/e) |
| δ = 4,30 | (t, 2H) | 43, 85, 101, 59, 41, 39, 100, 99, 45, 42 |

(i) Preparation of 2,5-dimethyl-3-(2'-methyl-2'-tetrahydrothienylthio)-4,5-dihydrofuran (II; $R_1=CH_3$, $R_2=CH_3$, $R_3=CH_3$, $R_4=H$, $X=O$, $Y=S$)

Addition reaction of 4,5-dihydro-2,5-dimethyl-3-mercaptofuran and 4,5-dihydro-2-methylthiophene.

Spectral data of the title compound (mixture of isomers) after purification by liquid chromatography:

| NMR spectrum (δ in ppm) | | |
|---|---|---|
| δ = 1,34 | (d, 3H) | IR spectrum |
| δ = 1,70 | (s, 3H) | 2970, 2920, 2860, 1630, 1438, 1375, 1330, |
| δ = 1,88 | (t, 3H) | 1220, 1190, 1129, 1053, 1021, 956, 900, |
| δ = 1,8–3,2 | (m, 8H) | 820, 656, 568, 508, 498 cm$^{-1}$ |
| δ = 4,6 | (m, 1H) | MS spectrum (m/e) |
| | | 43, 85, 100, 59, 99, 101, 130, 128, 45, 39 |

(j) Preparation of 2-methyl-3-(2',5'-dimethyl-2'-tetrahydrofurylthio)furan (III; $R_1=CH_3$, $R_2=H$, $R_3=CH_3$, $R_4=CH_3$, $X=O$, $Y=O$)

Addition reaction of 2-methyl-3-mercaptofuran and 4,5-dihydro-2,5-dimethylfuran.

Spectral data of isomers 1 and 2 after purification by liquid chromatography:

| NMR spectrum (δ in ppm) | | | |
|---|---|---|---|
| 1 | δ = 1,22 | (d, 3H) | IR spectrum |
| | δ = 1,45 | (s, 3H) | 3145, 3120, 2970, 2920, 2865, 1580, |
| | δ = 1,8–2,2 | (m, 4H) | 1510, 1441, 1382, 1369, 1220, 1189, |
| | δ = 2,33 | (s, 3H) | 1080, 1030, 961, 939, 888, 825, |
| | δ = 4,32 | (m, 1H) | 730, 656, 606, 545, 515, 492, cm |
| | δ = 6,28 | (d, 1H) | MS spectrum (m/e) |
| | δ = 7,22 | (d, 1H) | 43, 114, 98, 83, 55, 85, 39, 113, 53, 54 |
| 2 | δ = 1,29 | (d, 3H) | IR spectrum |
| | δ = 1,45 | (s, 3H) | 3115, 2970, 2920, 2860, 1580, 1511, |
| | δ = 1,7–2,2 | (m, 4H) | 1438, 1383, 1368, 1220, 1202, 1189, |
| | δ = 2,34 | (s, 3H) | 1104, 1084, 1022, 958, 940, 888, |
| | δ = 4,15 | (m, 1H) | 825, 800, 730, 653, 605, 560, 502 cm |
| | δ = 6,34 | (d, 1H) | MS spectrum (m/e) |
| | δ = 7,22 | (d, 1H) | 43, 114, 83, 98, 55, 39, 53, 85, 41, 45 |

(k) Preparation of 2,5-dimethyl-3-(2',5'-dimethyl-2'-tetrahydrofurylthio)-tetrahydrofuran (I; $R_1=CH_3$, $R_2=CH_3$, $R_3=CH_3$, $R_4=CH_3$, $X=O$, $Y=O$)

Addition reaction of 2,5-dimethyl-3-mercaptotetrahydrofuran (mixture of isomers) and 4,5-dihydro-2,5-dimethylfuran.

Spectral data of the mixtures of isomers 1, 2 and 3 after purification by liquid chromatography:

| NMR spectrum (δ in ppm) | | | |
|---|---|---|---|
| 1 | δ = 1,17 | (d, 3H) | IR spectrum |
| | δ = 1,21 | (d, 3H) | 2970, 2930, 2870, 1444, |
| | δ = 1,25 | (d, 3H) | 1375, 1194, 1163, 1142, |
| | δ = 1,65 | (s, 3H) | 1106, 1078, 963, 950, 942, |
| | δ = 1,8–2,2 | (m, 6H) | 883, 829, 559 cm$^{-1}$ |
| | δ = 2,8 | (m, 1H) | MS spectrum (m/e) |
| | δ = 3,5 | (m, 1H) | 55, 43, 54, 98, 88, |
| | δ = 3,8–4,4 | (m, 2H) | 99, 83, 39, 73, 60 |
| 2 | δ = 1,0–1,20 | (doublets, 9H) | IR spectrum |
| | δ = 1,62 (s) ⎫ 3H | | 2970, 2930, 2865, 1444, |
| | δ = 1,65 (s) ⎭ | | 1375, 1193, 1142, 1105, |
| | δ = 1,8–2,2 | (m, 6H) | 1079, 962, 942, 883, 828, |
| | δ = 3,35 | (m, 1H) | 810, 559 cm$^{-1}$ |
| | δ = 3,9–4,2 | (m, 3H) | MS spectrum (m/e) |
| | | | 55, 43, 98, 54, 88, |
| | | | 99, 83, 73, 39, 60 |
| 3 | δ = 1,13 | (d, 3H) | IR spectrum |
| | δ = 1,19 | (d, 6H) | 2970, 2930, 2870, 1444, |
| | δ = 1,60 ⎫ (s, 3H) | | 1376, 1190, 1143, 1105, |
| | δ = 1,63 ⎭ | | 1080, 961, 942, 884, 828, 558 cm$^{-1}$ |

-continued

| NMR spectrum (δ in ppm) | | |
|---|---|---|
| δ = 1,8–2,5 | (m, 6H) | MS spectrum (m/e) |
| δ = 3,2–4,3 | (m, 4H) | 55, 43, 54, 98, 88, 99, 83, 73, 39, 60 |

(l) Preparation of 2,5-dimethyl-3-(2',5'-dimethyl-2'-tetrahydrofurylthio)furan (III; $R_1=CH_3$, $R_2=CH_3$, $R_3=CH_3$, $R_4=CH_3$, X=O, Y=O)

Addition reaction of 2,5-dimethyl-3-mercaptofuran and 4,5-dihydro-2,5-dimethylfuran Spectral data of isomers 1 and 2 after purification by liquid chromatography:

| NMR spectrum (δ in ppm) | | |
|---|---|---|
| 1 δ = 1,22 | (d, 3H) | IR spectrum |
| δ = 1,46 | (s, 3H) | 3105, 2970, 2920, 2865, 1607, 1570, |
| δ = 1,9–2,2 | (m, 4H) | 1440, 1379, 1369, 1332, 1220, 1108, |
| δ = 2,25 | (s, 3H) | 1080, 1064, 960, 941, 922, 884, |
| δ = 2,28 | (s, 3H) | 824, 800, 653, 616 cm$^{-1}$ |
| δ = 4,37 | (m, 1H) | MS spectrum (m/e) |
| δ = 5,88 | (s, 1H) | 43, 98, 83, 39, 55, 41, 42, 128, 85, 127 |
| 2 δ = 1,24 | (d, 3H) | IR spectrum |
| δ = 1,48 | (s, 3H) | 3110, 2970, 2925, 2870, 1608, 1570, |
| δ = 1,8–2,2 | (m, 4H) | 1440, 1380, 1370, 1333, 1220, 1109, |
| δ = 2,30 | (s, 6H) | 1064, 1003, 986, 960, 942, 922, |
| δ = 4,30 | (m, 1H) | 884, 824, 800, 653, 616, 550, 483, cm$^{-1}$ |
| δ = 5,88 | (s, 1H) | MS spectrum |
| | | 43, 128, 98, 83, 55, 39, 42, 41, 127, 85 |

EXAMPLE 3

Preparation of 2-methyl-1-(2'-methyl-2'-tetrahydrofurylthio)cyclopentane (I; $R_1=CH_3$, $R_2=H$, $R_3=CH_3$, $R_4=H$, $X=CH_2$, Y=O)

In a three-necked 250 ml round bottomed flask provided with a mechanical stirrer, dropping funnel, reflux condenser and thermometer are placed 5.04 g (0.060 mole) of 4,5-dihydro-2-methylfuran in 40 ml of pentane and a trace of p-toluenesulfonic acid. The reaction is carried out under nitrogen. The stirrer is started and 7.00 g (0.060 mole) of 2-methyl-1-mercaptocyclopentane (mixture of cis and trans isomer) in 15 ml of pentane is added in 30 minutes. The reaction mixture is heated and allowed to reflux for four hours.

After cooling to room temperature the reaction mixture is washed twice with 20 ml of water and dried over anhydrous sodium sulfate. Distillation gives the title compound as a mixture of cis and trans isomers; bp. 75°–76° C./2 mm Hg.

Spectral data of the compound as a mixture of cis and trans isomers:

| NMR spectrum (δ in ppm) | | |
|---|---|---|
| δ = 0,94 | (d, 3H) | IR spectrum |
| δ = 1,64 | (s, 3H) | 2960, 2865, 1451, 1440, 1372, 1351, 1314, |
| δ = 1,5–2,3 | (m, 11H) | 1301, 1236, 1188, 1136, 1100, 1036, |
| δ = 3,21 | (m, 1H) | 1019, 923, 901, 833, 566 cm$^{-1}$ |
| δ = 3,78 | (m, 2H) | MS spectrum (m/e) |
| | | 43, 55, 83, 41, 39, 67, 84, 60, 53, 116 |

According to the procedure described in Example 3 the following compounds have been prepared:

(a) Preparation of 2,5-dimethyl-3-(2'-methyl-2'-tetrahydrothienylthio)tetrahydrofuran (I; $R_1=CH_3$, $R_2=CH_3$, $R_3=CH_3$, $R_4=H$, X=O, Y=S)

Addition reaction of 2,5-dimethyl-3-mercaptotetrahydrofuran and 4,5-dihydro-2-methylthiophene.

Spectral data of the mixtures of isomers 1 and 2 after purification by liquid chromatography:

| NMR spectrum (δ in ppm) | | |
|---|---|---|
| 1 δ = 1,18 | (d, 3H) | IR spectrum |
| δ = 1,28 | (d, 3H) | 2965, 2925, 2860, 1440, 1372, |
| δ = 1,75 | (s, 3H) | 1162, 1118, 1069, 1056, 948, |
| δ = 1,8–2,4 | (m, 6H) | 918, 879, 732, 666 cm$^{-1}$ |
| δ = 2,6–3,2 | (m, 3H) | MS spectrum (m/e) |
| δ = 3,4 | (m, 1H) | 55, 85, 100, 99, 59, 88, 43, 54, |
| δ = 3,95 | (m, 1H) | 45, 39 |
| 2 δ = 1,05–1,30 | (doublets, 6H) | IR spectrum |
| δ = 1,78 | (s, 3H) | 2970, 2925, 2860, 1440, 1374, |
| δ = 1,9–2,5 | (m, 6H) | 1263, 1114, 1105, 1073, 1020, |
| δ = 2,9–3,5 | (m, 3H) | 947, 915, 880, 810, 666 cm$^{-1}$ |
| δ = 4,2 | (m, 2H) | MS spectrum (m/e) |
| | | 55, 43, 85, 100, 99, 59, 42, 41, 54, 39 |

(b) Preparation of 2,5-dimethyl-3-(2'-methyl-2'-tetrahydrothienylthio)furan (III; $R_1=CH_3$, $R_2=CH_3$, $R_3=CH_3$, $R_4=H$, X=O, Y=S)

Addition reaction of 2,5-dimethyl-3-mercaptofuran and 4,5-dihydro-2-methylthiophene.

Spectral data after purification by liquid chromatography:

| NMR spectrum (δ in ppm) | | |
|---|---|---|
| δ = 1,65 | (s, 3H) | IR spectrum |
| δ = 2,24 | (s, 3H) | 3105, 2950, 2920, 2855, 1606, 1565, |
| δ = 2,31 | (s, 3H) | 1436, 1377, 1369, 1332, 1304, 1220, |
| δ = 1,8–2,5 | (m, 4H) | 1128, 1114, 1064, 1054, 985, 923, |
| δ = 3,0, | (m, 2H) | 800, 656, 616, 485, 470 cm$^{-1}$ |
| δ = 5,92 | (s, 1H) | MS spectrum (m/e) |
| | | 85, 128, 43, 100, 99, 59, 101, 127, 39, 41 |

(c) Preparation of 2-methyl-3-(2'-methyl-2'-tetrahydrothienylthio)tetrahydrothiophene (I; $R_1=CH_3$, $R_2=H$, $R_3=CH_3$, $R_4=H$, X=S, Y=S)

Addition reaction of 2-methyl-3-mercaptotetrahydrothiophene and 4,5-dihydro-2-methylthiophene.

Spectral data of the mixture of cis and trans isomers after purification by liquid chromatography:

| NMR spectrum (δ in ppm) | | |
|---|---|---|
| δ = 1,27 (d) | ⎫ 3H | IR spectrum |
| δ = 1,38 (d) | ⎭ | 2955, 2920, 2860, 1436, 1371, 1304, 1259, 1228, 1194, 1165, 1129, 1067, |
| δ = 1,80 | (s, 2H) | 1056, 1020, 886, 732, 684, 666 cm$^{-1}$ |
| δ = 1,9–2,5 | (m, 6H) | MS spectrum (m/e) |
| δ = 2,7–3,2 | (m, 6H) | 100, 85, 99, 59, 41, 39, 65, 58, 55, 101 |

(d) Preparation of 2-methyl-3-(2'-methyl-2'-tetrahydrothienylthio)-4,5-dihydrothiophene (II; $R_1=CH_3$, $R_2=H$, $R_3=CH_3$, $R_4=H$, $X=S$, $Y=S$)

Addition reaction of 4,5-dihydro-2-methyl-3-mercaptothiophene and 4,5-dihydro-2-methylthiophene.

Spectral data after purification by liquid chromatography:

| NMR spectrum ($\delta$ in ppm) | | |
|---|---|---|
| $\delta$ = 1,73 | (s, 3H) | IR spectrum |
| $\delta$ = 2,06 | (t, 3H) | 2950, 2855, 2840, 1582, 1436, 1369, 1260, |
| $\delta$ = 2,0–2,5 | (m, 4H) | 1144, 1125, 1053, 853, 748, 650, 426 cm$^{-1}$ |
| $\delta$ = 2,9–3,3 | (m, 6H) | MS spectrum (m/e) |
| | | 85, 59, 99, 100, 45, 39, 132, 65, 97, 58 |

(e) Preparation of 2-methyl-3-(2'-methyl-2'-tetrahydrothienylthio)thiophene (III; $R_1=CH_3$, $R_2=H$, $R_3=CH_3$, $R_4=H$, $X=S$, $Y=S$)

Addition reaction of 2-methyl-3-mercaptothiophene and 4,5-dihydro-2-methylthiophene Spectral data after purification by liquid chromatography:

| NMR spectrum ($\delta$ in ppm) | | |
|---|---|---|
| $\delta$ = 1,67 | (s, 3H) | IR spectrum |
| $\delta$ = 1,9–2,4 | (m, 4H) | 3100, 3070, 2960, 2920, 2860, 1436, 1370, |
| $\delta$ = 2,57 | (s, 3H) | 1304, 1261, 1226, 1174, 1128, 1055, 852, |
| $\delta$ = 2,98 | (m, 2H) | 710, 630, 478, 437 cm$^{-1}$ |
| $\delta$ = 6,97 | (s, 2H) | MS spectrum (m/e) |
| | | 130, 85, 100, 59, 99, 97, 43, 45, 129, 39 |

(f) Preparation of 2-methyl-3-(2'-5'-dimethyl-2'-tetrahydrofurylthio)tetrahydrofuran (I; $R_1=CH_3$, $R_2=H$, $R_3=CH_3$, $R_4=CH_3$, $X=O$, $Y=O$)

Addition reaction of 2-methyl-3-mercaptotetrahydrofuran and 4,5-dihydro-2,5-dimethylfuran.

Spectral data of the mixtures of isomers 1 and 2 after purification by liquid chromatography:

| NMR spectrum ($\delta$ in ppm) | | | |
|---|---|---|---|
| 1 | $\delta$ = 1,22 | (d, 6H) | IR spectrum |
| | $\delta$ = 1,65 | (s, 3H) | 2970, 2930, 2865, 1452, 1443, |
| | $\delta$ = 1,7–2,5 | (m, 6H) | 1378, 1371, 1352, 1191, 1141, |
| | $\delta$ = 2,8 | (m, 1H) | 1105, 1079, 1034, 1015, 963, |
| | $\delta$ = 3,2–3,9 | (m, 3H) | 941, 883, 860, 827, |
| | $\delta$ = 4,2 | (m, 1H) | 560, 472 cm$^{-1}$ |
| | | | MS spectrum (m/e) |
| | | | 43, 41, 74, 55, 39, |
| | | | 83, 45, 54, 53 |
| 2 | $\delta$ = 1,07 | (d, 3H) | IR spectrum |
| | $\delta$ = 1,20 | (d, 3H) | 2970, 2930, 2870, 1442, 1372, 1350, |
| | | | 1192, |
| | $\delta$ = 1,62 (s) ⎫ | | 1142, 1104, 1076, 1032, 962, 940, |
| | | ⎬ 3H | 882, |
| | $\delta$ = 1,64 (s) ⎭ | | 826 cm$^{-1}$ |
| | | | MS spectrum (m/e) |
| | $\delta$ = 1,8–2,4 | (m, 5H) | 43, 41, 74, 55, 98, 39, 83, 54, 45, 84 |
| | $\delta$ = 3,1–4,4 | (m, 6H) | |

(g) Preparation of 2-methyl-3-(2',5'-dimethyl-2'-tetrahydrofurylthio)-4,5-dihydrofuran (II; $R_1=CH_3$, $R_2=H$, $R_3=CH_3$, $R_4=CH_3$, $X=O$, $Y=O$)

Addition reaction of 4,5-dihydro-2-methyl-3-mercaptofuran and 4,5-dihydro-2,5-dimethylfuran.

Spectral data of the compound (mixture of isomers) after purification by liquid chromatography:

| NMR spectrum ($\delta$ in ppm) | | |
|---|---|---|
| $\delta$ = 1,18 | (d, 3H) | IR spectrum |
| $\delta$ = 1,53 | (s, 3H) | 2965, 2920, 2890, 2865, 1642, 1438, 1377, |
| $\delta$ = 1,84 | (t, 3H) | 1214, 1077, 982, 957, 938, 908, 882, 824, |
| $\delta$ = 1,8–2,2 | (m, 4H) | 548, 488 cm$^{-1}$ |
| $\delta$ = 2,8 | (m, 2H) | MS spectrum (m/e) |
| $\delta$ = 4,28 | (t, 2H) | 43, 83, 98, 55, 42, 41, 39, 114, 84, 54 |
| $\delta$ = 4,3 | (m, 1H) | |

(h) Preparation of 2,5-dimethyl-3-(2',5'-dimethyl-2'-tetrahydrofurylthio)-4,5-dihydro (II; $R_1=CH_3$, $R_2=CH_3$, $R_3=CH_3$, $R_4=CH_3$, $X=O$, $Y=O$)

Addition reaction of 4,5-dihydro-2,5-dimethyl-3-mercaptofuran and 4,5-dihydro-2,5-dimethylfuran.

Spectral data of the mixtures of isomers 1 and 2 after purification by liquid chromatography:

| NMR spectrum ($\delta$ in ppm) | | | |
|---|---|---|---|
| 1 | $\delta$ = 1,23 | (d, 3H) | IR spectrum |
| | $\delta$ = 1,35 | (d, 3H) | 2970, 2925, 2865, 1644, 1442, 1376, |
| | $\delta$ = 1,54 | (s, 3H) | 1329, 1219, 1192, 1142, 1100, 1080, |
| | $\delta$ = 1,85 | (t, 3H) | 1031, 1023, 956, 940, 884, 824, |
| | $\delta$ = 1,8–3,2 | (m, 6H) | 571, 550, 500 cm$^{-1}$ |
| | $\delta$ = 4,0–4,9 | (m, 2H) | MS spectrum (m/e) |
| | | | 43, 98, 83, 55, 130, 39, 128, 54, 53, 97 |
| 2 | $\delta$ = 1,32 | (d, 6H) | IR spectrum |
| | $\delta$ = 1,50 | (s, 3H) | 2970, 2925, 2865, 1643, 1442, 1375, |
| | $\delta$ = 1,85 | (t, 3H) | 1329, 1220, 1190, 1142, 1101, 1064, |
| | $\delta$ = 1,8–3,2 | (m, 6H) | 1024, 955, 885, 822, 801, 648, |
| | $\delta$ = 4,0–4,9 | (m, 2H) | 557, 505 cm$^{-1}$ |
| | | | MS spectrum (m/e) |
| | | | 43, 98, 83, 55, 130, 39, 128, 54, 53, 97 |

(i) Preparation of 2-methyl-3-(2'-5'-dimethyl-2'-tetrahydrofurylthio)tetrahydrothiophen (I; $R_1=CH_3$, $R_2=H$, $R_3=CH_3$, $R_4=CH_3$, $X=S$, $Y=O$)

Addition reaction of 2-methyl-3-mercaptotetrahydrothiophene and 4,5-dihydro-2,5-dimethylfuran.

Spectral data of the mixtures of isomers 1 and 2 after purification by liquid chromatography:

| NMR spectrum ($\delta$ in ppm) | | | |
|---|---|---|---|
| 1 | $\delta$ = 1,22 | (d, 3H) | IR spectrum |
| | $\delta$ = 1,35 | (doublets, 3H) | 2970, 2925, 2865, 1453, 1442, |
| | $\delta$ = 1,65 | (singlets, 3H) | 1371, 1191, 1144, 1103, 1078, |
| | $\delta$ = 1,95 | (m, 6H) | 1033, 960, 940, |
| | $\delta$ = 2,7–3,1 | (m, 4H) | 883, 828, 68, 558 cm$^{-1}$ |
| | $\delta$ = 4,25 | (m, 1H) | MS spectrum (m/e) |
| | | | 43, 55, 98, 83, 39, |
| | 41, 134, 54, | | |
| | 53, 74 | | |
| 2 | $\delta$ = 1,22 | (d, 3H) | IR spectrum |
| | $\delta$ = 1,3 | (doublets, 3H) | 2960, 2920, 2865, 1452, 1443, |
| | $\delta$ = 1,67 | (s, 3H) | 1370, 1194, 1142, 1101, 1076, |
| | $\delta$ = 1,8–2,4 | (m, 5H) | 1033, 1023, 959, 940, 884, |

| NMR spectrum (δ in ppm) | | |
|---|---|---|
| δ = 2,8 | (m, 3H) | 826, 802, 683, 675, 556 cm$^{-1}$ |
| δ = 3,4 | (m, 2H) | MS spectrum (m/e) |
| δ = 4,2 | (m, 1H) | 43, 55, 39, 98, 41, 83, 134, 54, 53, 47 |

(j) Preparation of 2-methyl-3-(2',5'-dimethyl-2'-tetrahydrofurylthio)-4,5-dihydrothiophene (II; $R_1$=CH$_3$, $R_2$=H, $R_3$=CH$_3$, $R_4$=CH$_3$, X=S, Y=O)

Addition reaction of 4,5-dihydro-2-methyl-3-mercaptothiophene and 4,5-dihydro-2,5-dimethylfuran.

Spectral data of the mixtures of isomers 1 and 2 after purification by liquid chromatography:

| NMR spectrum (δ in ppm) | | | |
|---|---|---|---|
| 1 | δ = 1,25 | (d, 3H) | IR spectrum |
| | δ = 1,46 | (s, 3H) | 2965, 2920, 2865, 1591, 1439, 1380, |
| | δ = 2,00 | (t, 3H) | 1370, 1296, 1191, 1144, 1106, 1079, |
| | δ = 1,9–2,3 | (m, 4H) | 1030, 960, 939, 883, |
| | δ = 3,1 | (m, 4H) | 823, 750, 556, 524 cm$^{-1}$ |
| | δ = 4,32 | (m, 1H) | MS spectrum (m/e) |
| | | | 43, 98, 99, 83, 55, 39, 132, 97, 59, 41 |
| 2 | δ = 1,35 | (d, 3H) | IR spectrum |
| | δ = 1,52 | (s, 3H) | 2965, 2925, 2865, 1591, 1440, 1370, |
| | δ = 2,00 | (t, 3H) | 1203, 1145, 1104, 1061, 1024, 959, |
| | δ = 1,8–2,3 | (m, 4H) | 884, 823, 801, 761, 562, |
| | δ = 3,1 | (m, 4H) | 519 cm$^{-1}$ |
| | δ = 4,17 | (m, 1H) | MS spectrum (m/e) |
| | | | 43, 99, 98, 39, 55, 83, 132, 97, 41, 59 |

(k) Preparation of 1-(2'-methyl-2'-tetrahydrofurylthio)cyclopentane (I; $R_1$=H, $R_2$=H, $R_3$=CH$_3$, $R_4$=H, X=CH$_2$, Y=O)

Addition reaction of mercaptocyclopentane and 4,5-dihydro-2-methylfuran.

Spectral data of the title compound:

| NMR spectrum (δ in ppm) | | |
|---|---|---|
| δ = 1,64 | (s, 3H) | IR spectrum |
| δ = 1,6–2,2 | (m, 12H) | 2960, 2870, 1450, 1442, 1370, 1350, 1314, |
| δ = 3,1 | (m, 1H) | 1298, 1234, 1189, 1137, 1100, 1038, 1020, |
| δ = 3,87 | (m, 2H) | 923, 902, 8, 565 cm$^{-1}$ |
| | | MS spectrum (m/e) |
| | | 69, 43, 41, 39, 84, 102, 68, 67, 83, 60 |

(l) Preparation of 2-methyl-1-(2'-methyl-2'-tetrahydrofurylthio)-1-cyclopentene (II; $R_1$=CH$_3$, $R_2$=H, $R_3$=CH$_3$, $R_4$=H, X=CH$_2$, Y=O)

Addition reaction of 2-methyl-1-mercaptocyclopentene-1 and 4,5-dihydro-2-methylfuran.

Spectral data of the title compound:

| NMR spectrum (δ in ppm) | | |
|---|---|---|
| δ = 1,53 | (s, 3H) | IR spectrum |
| δ = 1,70 | (s, 3H) | 2970, 2950, 2925, 2880, 1628, 1438, 1371, |
| δ = 1,5–2,7 | (m, 10H) | 1350, 1314, 1287, 1230, 1186, 1136, 1103, |
| δ = 3,87 | (m, 2H) | 1037, 1019, 989, 922, 902, 834, 563, 527 cm$^{-1}$ |
| | | MS spectrum (m/e) |
| | | 81, 43, 39, 114, 84, 79, 41, 55, 53, 83 |

(m) Preparation of 2-ethyl-1-(2'-methyl-2'-tetrahydrofurylthio)cyclopentane (I; $R_1$=C$_2$H$_5$, $R_2$=H, $R_3$=CH$_3$, $R_4$=H, X=CH$_2$, Y=O)

Addition reaction of 2-ethyl-1-mercaptocyclopentane (mixture of cis and trans isomer) and 4,5-dihydro-2-methylfuran.

Spectral data of the title compound as a mixture of cis and trans isomers:

| NMR spectrum (δ in ppm) | | |
|---|---|---|
| δ = 0,9 | (broad t, 3H) | IR spectrum |
| δ = 1,61 | (s, 3H) | 2955, 2870, 1455, 1371, 1350, |
| δ = 1,1–2,1 | (m, 13H) | 1329, 1189, 1137, 1098, 1038, |
| δ = 2,55 | } (m, 1H) | 1020, 921, 901, 830, 562 cm$^{-1}$ |
| | | MS spectrum (m/e) |
| δ = 3,15 | | 67, 43, 55, 41, 39, |
| δ = 3,8 | (m, 2H) | 97, 130, 84, 60, 53 |

(n) Preparation of 1-(2'-methyl-2'-tetrahydrofurylthio)-1-cyclopentene (II; $R_1$=H, $R_2$=H, $R_3$=CH$_3$, $R_4$=H, X=CH$_2$, Y=O)

Addition reaction of 1-mercaptocyclopentene-1 and 4,5-dihydro-2-methylfuran.

Spectral data of the title compound:

| NMR spectrum (δ in ppm) | | |
|---|---|---|
| δ = 1,77 | (s, 3H) | IR spectrum (in CCl$_4$) |
| δ = 1,4–2,7 | (m, 10H) | 2960, 2860, 1680, 1439, 1369, 1310, 1290, |
| δ = 3,95 | (m, 2H) | 1200, 1134, 1100, 1036, 1018, 976, 920, |
| δ = 5,78 | (m, 1H) | 902, 559 cm$^{-1}$ |
| | | MS spectrum (m/e) |
| | | 43, 39, 84, 41, 83, 69, 67, 55, 53, 54 |

EXAMPLE 4

An instant beef gravy powder was prepared from the following ingredients:

| | % |
|---|---|
| spray-dried vegetable oil base powder | 20.0 |
| spice extract powder | 0.2 |
| spray-dried tomato powder | 7.0 |
| sodium chloride | 12.0 |
| mono sodium glutamate | 8.0 |
| hydrolysed vegetable protein (Hercules Protex 14) | 6.0 |
| caramel powder | 1.5 |
| granulated sugar | 3.0 |
| modified potato starch | 25.0 |
| autolysed yeast powder | 5.0 |
| carboxy methyl cellulose | 0.8 |
| non fat dry milk solids | 11.5 |
| Total dry matter | 100.0 |

60 grams of this mixture were dissolved in 940 grams of boiling water, thus giving 1 kg of gravy. The gravy so obtained was divided into two portions of 500 g each. To one of the portions 0.25 g of a 0.3% solution of compound 3f (isomeric mixture 2) in ethanol was added and the mixture was well stirred. The level of the said compound in the gravy can be expressed as 1.5 ppm. Both gravies were compared by a panel of qualified testers. The gravy containing the said compound was definitely preferred by the majority of the testers, since it was found to possess a well recognizable beef note which was absent in the gravy without the said compound.

EXAMPLE 5

One and a half kg of gravy was prepared according to the method described in Example 4. The gavy was divided into three portions of 500 grams each. To one of the portions 0.10 g of a 0.3% solution of compound 2d in ethanol was added. This mixture is called mixture A. To a second portion of the gravy 0.10 grams of a 0.3% solution of compound 3i (isomeric mixture 1) in ethanol was added. This mixture is called mixture B. Both mixtures A and B were well stirred. Mixtures A and B were panel tested against the 'control' which was the gravy without the additions described above. The panel showed a clear preferance for mixtures A and B over the control. Mixture A was described as having a cooked meat note, whereas Mixture b was described to possess a more general beef note.

EXAMPLE 6

Compound 2d is dissolved in ethanol to provide a 0.1% solution. This solution in the amount of 0.175 g is added to 80 grams of a clear beef broth. The level of compound 2d in the broth can be expressed as 2.1 ppm. On simmering the broth containing compound 2d for 10 minutes, it was found by a test panel that it possessed increased beef taste and odor, in comparison with the same broth also simmered for 10 minutes but not containing compound 2d.

EXAMPLE 7

Compound 2d is dissolved in ethanol to provide a 0.1% solution. This solution in the amount of 0.2 grams is added to 80 grams of a commercial grade of canned gravy. The level of compound 2d in the gravy can be expressed as 2.4 ppm. The gravy containing compound 2d and the same quantity of the gravy not containing this compound were autoclaved during 15 minutes at 120° C. After this treatment, the gravy containing compound 2d was found (by a test panel) to possess a definitely increased beef note, when compared with the gravy not containing compound 2d.

EXAMPLE 8

To 100 grams of warm gravy, as described in Example 4, 0.2 gram of a 0.1% solution of compound 3 in ethanol was added. The level of compound 3 in the gravy can be expressed as 2 ppm. The mixture thus obtained was panel tested against a sample of the same gravy not containing compound 3. The panel was unanimously in its preference for the gravy containing compound 3, since this mixture was found to possess a well recognizable meaty note, which was absent in the gravy not containing compound 3. A similar effect was obtained with compound 1c (cis-isomers) when the dosage was 0.4 grams of a 0.1% solution in 100 grams of gravy (4 ppm).

EXAMPLE 9

A meatless imitation Hamburger patties base have been prepared by mixing the following ingredients:

| | |
|---|---|
| textured vegetable protein | 25.0% |
| water | 50.0 |
| sodium chloride | 2.0 |
| mono sodium glutamate | 0.5 |
| hydrolysed vegetable protein | 0.5 |
| autolysed yeast extract | 0.5 |
| instant rice starch | 5.0 |
| hydrogenated vegetable oil | 5.0 |
| whole fresh egg | 2.5 |
| dehydrated bread crumbs | 5.0 |
| sodium caseinate | 2.5 |
| spray dried tomato powder | 1.0 |
| spice extract powder | 0.5 |
| | 100.0% |

To 1 kg of the base, a solution of 0.3% of compound 3f (isomeric mixture 2) was added in the amount of 12.5 grams. Of this mixture and of the base without the said compound Hamburger-like patties were made and fried in margarine. The fried patties with the said compound were panel-tested against the controls without the compound and were found to have a good meat-like odor and taste.

In a similar experiment, to 1 kg of the imitation Hamburger base 2.8 grams of a 0.3% solution of compound 3i (isomeric mixture 1) in ethanol was added. The fried patties with the said compound were found to possess an excellent meat-like taste.

In a similar experiment, to 1 kg of the imitation Hamburger base 1.6 gram of a 0.3% solution of compound 3 in ethanol was added. The fried patties with compound 3 were found to possess a well recognizable meaty and slightly onion-like taste.

In a similar experiment to 1 kg of the imitation Hamburger base 5.3 g of a 0.3% solution of compound 2d in ethanol was added. The fried patties with compound 2d were found to possess a good meaty note when compared with the patties without compound 2d.

What we claim and desire to protect by Letters Patent is:

1. A chemical compound having the structural formula:

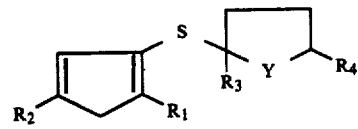

wherein
the five carbon ring is a cyclopentane ring or a $\Delta^{2,3}$-cyclopentene ring;
Y is oxygen or sulfur; and $R_1$, $R_2$, $R_3$ and $R_4$ are hydrogen or 1 to 3 carbon alkyl groups.

2. A chemical compound having the structural formula:

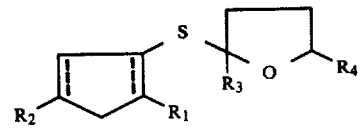

wherein
the five carbon ring is a cyclopentane ring or a $\Delta^{2,3}$-cyclopentene ring; and $R_1$, $R_2$, $R_3$, and $R_4$ are hydrogen or 1 to 3 carbon alkyl groups.

3. (2'-methyl-2'-tetrahydrofurylthio)cyclopentane.
4. 2-methyl-1-(2'-methyl-2'-tetrahydrofurylthio)cyclopentane.
5. 2-ethyl-1-(2'-methyl-2'-tetrahydrofurylthio)cyclopentane.
6. (2'-methyl-2'-tetrahydrofurylthio)-1-cyclopentene.
7. 2-methyl-1-(2'-methyl-2'-tetrahydrofurylthio)-1-cyclopentene.
8. A chemical compound have the structural formula

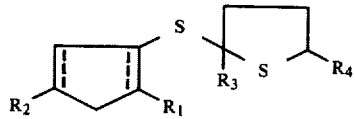

wherein
  the five carbon ring is a pentane ring or a $\Delta^{2,3}$-cyclopentene ring, and
  $R_1$, $R_2$, $R_3$, and $R_4$ are hydrogen or 1 to 3 carbon alkyl groups.

* * * * *